(12) United States Patent
Bailey et al.

(10) Patent No.: US 10,709,520 B2
(45) Date of Patent: *Jul. 14, 2020

(54) END EFFECTOR FOR A POSITIONING DEVICE

(71) Applicant: SYNAPTIVE MEDICAL (BARBADOS) INC., Bridgetown (BB)

(72) Inventors: Brent Andrew Bailey, Toronto (CA); Mariana Garcia Coni, Toronto (CA)

(73) Assignee: Synaptive Medical (Barbados) Inc., Bridgetown (BB)

( * ) Notice: Subject to any disclaimer, the term of this patent is extended or adjusted under 35 U.S.C. 154(b) by 63 days.

This patent is subject to a terminal disclaimer.

(21) Appl. No.: 16/044,959

(22) Filed: Jul. 25, 2018

(65) Prior Publication Data

US 2018/0344426 A1 Dec. 6, 2018

Related U.S. Application Data

(63) Continuation of application No. 14/903,992, filed as application No. PCT/CA2014/050874 on Sep. 15, 2014, now Pat. No. 10,070,940.

(51) Int. Cl.
| | | |
|---|---|---|
| H04N 5/00 | (2011.01) |
| A61B 90/57 | (2016.01) |
| A61B 34/30 | (2016.01) |
| A61B 90/10 | (2016.01) |
| A61B 90/25 | (2016.01) |
| A61B 34/20 | (2016.01) |
| A61B 90/50 | (2016.01) |

(Continued)

(52) U.S. Cl.
CPC .............. *A61B 90/57* (2016.02); *A61B 34/20* (2016.02); *A61B 34/30* (2016.02); *A61B 90/10* (2016.02); *A61B 90/20* (2016.02); *A61B 90/25* (2016.02); *A61B 90/50* (2016.02); *H04N 5/2253* (2013.01); *H04N 5/23203* (2013.01); *A61B 2034/2055* (2016.02); *A61B 2090/306* (2016.02); *A61B 2090/3735* (2016.02); *A61B 2090/3983* (2016.02); *A61B 2090/571* (2016.02)

(58) Field of Classification Search
CPC ....... A61B 6/00; A61B 5/0071; A61B 5/0084; A61B 5/0086; A61B 5/14551; A61B 5/0059; A61B 5/0075; A61B 5/40; A61B 90/57; A61B 34/20; A61B 34/30; A61B 90/10; A61B 90/20; A61B 90/25; A61B 90/50; A61B 2034/2055; A61B 2090/306; A61B 2090/3735; A61B 2090/3983; A61B 2090/571; G01J 3/40; G01J 3/02; G01J 3/0208; G01J 3/021; G01J 3/0229; G01J 3/0264; G01J 3/282; G01J 3/10; G01J 3/2803; H04N 5/2253; H04N 5/23203

See application file for complete search history.

(56) References Cited

U.S. PATENT DOCUMENTS

| | | | | |
|---|---|---|---|---|
| 2010/0056928 A1* | 3/2010 | Zuzak | .................. | A61B 5/0071 600/476 |
| 2011/0130627 A1* | 6/2011 | McGrail | ............ | A61B 1/00016 600/109 |

* cited by examiner

*Primary Examiner* — Frank F Huang
(74) *Attorney, Agent, or Firm* — Rideout & Maybee LLP

(57) ABSTRACT

An end effector is provided for connecting to a positioning arm of a positioning device of a medical navigation system. The end effector comprises a mating component for connecting to an output flange of the positioning arm, a handle portion having a first end and a second end, the first end extending from the mating component, the handle portion including a cable cut-out at the first end, and a camera mount connected to the second end of the handle portion.

14 Claims, 11 Drawing Sheets

(51) Int. Cl.
A61B 90/20 (2016.01)
H04N 5/225 (2006.01)
H04N 5/232 (2006.01)
A61B 90/00 (2016.01)
A61B 90/30 (2016.01)

END EFFECTOR FOR A POSITIONING DEVICE

CROSS-REFERENCE TO RELATED APPLICATIONS

The present disclosure is a continuation of U.S. patent application Ser. No. 14/903,992, filed Jan. 8, 2016, which is a national phase entry of PCT application no. PCT/CA2014/050874, filed Sep. 15, 2014, the entireties of which are all incorporated by reference.

TECHNICAL FIELD

The present disclosure is generally related to image guided medical procedures, and more specifically to an end effector for a medical procedure positioning device employing a dynamic positioning system.

BACKGROUND

The present disclosure is generally related to image guided medical procedures using a surgical instrument, such as an optical scope, an optical coherence tomography (OCT) probe, a micro ultrasound transducer, an electronic sensor or stimulator, or an access port based surgery.

In the example of a port-based surgery, a surgeon or robotic surgical system may perform a surgical procedure involving tumor resection in which the residual tumor remaining after is minimized, while also minimizing the trauma to the intact white and grey matter of the brain. In such procedures, trauma may occur, for example, due to contact with the access port, stress to the brain matter, unintentional impact with surgical devices, and/or accidental resection of healthy tissue. A key to minimizing trauma is ensuring that the surgeon performing the procedure has the best possible view of the surgical site of interest without having to spend excessive amounts of time and concentration repositioning tools and cameras during the medical procedure.

FIG. 1 illustrates the insertion of an access port into a human brain, for providing access to internal brain tissue during a medical procedure. In FIG. 1, access port 12 is inserted into a human brain 10, providing access to internal brain tissue. Access port 12 may include such instruments as catheters, surgical probes, or cylindrical ports such as the NICO Brain Path. Surgical tools and instruments may then be inserted within the lumen of the access port in order to perform surgical, diagnostic or therapeutic procedures, such as resecting tumors as necessary. The present disclosure applies equally well to catheters, DBS needles, a biopsy procedure, and also to biopsies and/or catheters in other medical procedures performed on other parts of the body.

In the example of a port-based surgery, a straight or linear access port 12 is typically guided down a sulci path of the brain. Surgical instruments would then be inserted down the access port 12.

Optical tracking systems, used in the medical procedure, track the position of a part of the instrument that is within line-of-site of the optical tracking camera. These optical tracking systems also require a reference to the patient to know where the instrument is relative to the target (e.g., a tumor) of the medical procedure. These optical tracking systems require a knowledge of the dimensions of the instrument being tracked so that, for example, the optical tracking system knows the position in space of a tip of a medical instrument relative to the tracking markers being tracked. This enables a camera system that focuses on the surgical site of interest to display an image of the surgical site on a monitor so that the surgeon can see the surgical site at the end of the access port.

Conventional systems have not offered robust automated camera systems that maintain a field of view of the camera on the surgical site. Consequently, the choice of end effectors for robotic camera tracking systems is limited. It would be desirable to have an end effector for a medical procedure positioning device that satisfies the needs of operating room in the context of the procedures mentioned above.

SUMMARY

One aspect of the present disclosure provides an end effector for connecting to a positioning arm of a positioning device of a medical navigation system. The end effector comprises a mating component for connecting to an output flange of the positioning arm, a handle portion having a first end and a second end, the first end extending from the mating component, the handle portion including a cable cut-out at the first end, and a camera mount connected to the second end of the handle portion. The end effector may further have a mechanical interface located at the second end of the handle portion and a scope clamp arm connected to the mechanical interface for clamping a scope.

Another aspect of the present disclosure provides a medical navigation system having a positioning device having a positioning arm with an output flange at the end of the positioning arm, a controller at least electrically coupled to the positioning device, the controller having a processor coupled to a memory and a display, and an end effector connected to the positioning arm of the positioning device. The end effector comprises a mating component connected to the output flange, a handle portion having a first end and a second end, the first end extending from the mating component, the handle portion including a cable cut-out at the first end, and a camera mount connected to the second end of the handle portion.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Figure 1:
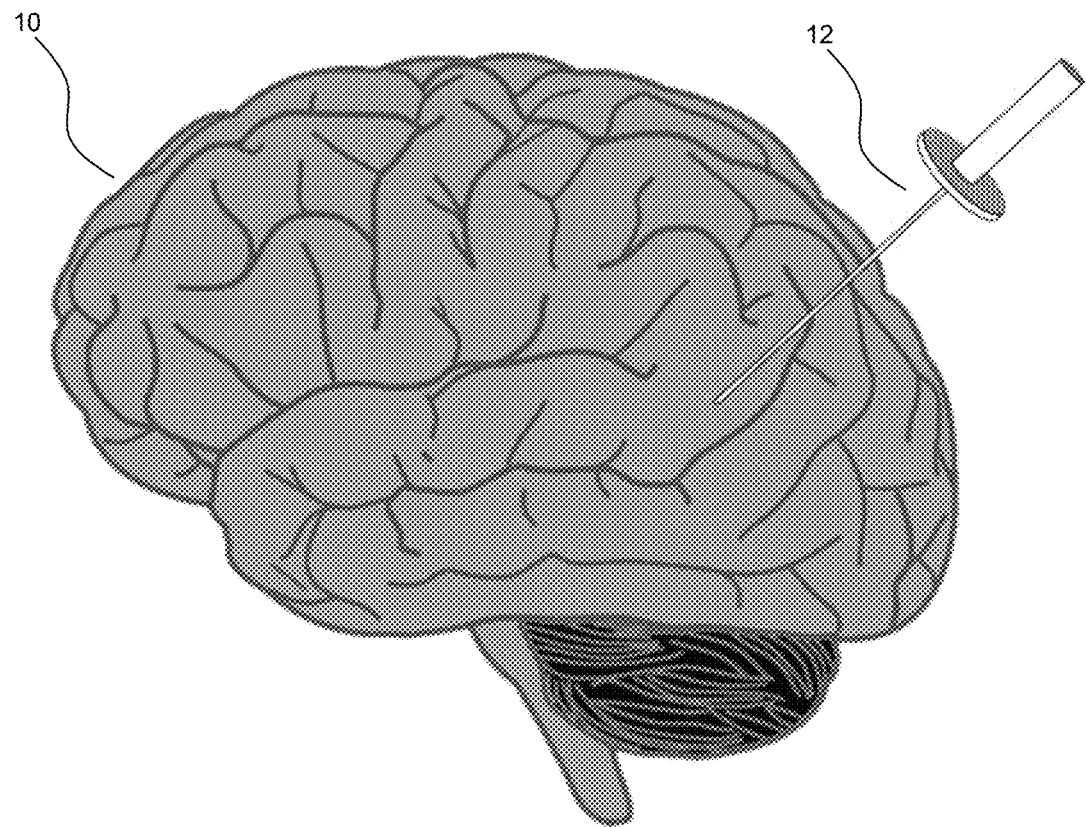
FIG. 1 illustrates the insertion of an access port into a human brain, for providing access to internal brain tissue during a medical procedure.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about", "approximately", and "substantially" are meant to cover variations that may exist in the upper and lower limits of the ranges of values, such as variations in properties, parameters, and dimensions. In one non-limiting example, the terms "about", "approximately", and "substantially" mean plus or minus 10 percent or less.

Unless defined otherwise, all technical and scientific terms used herein are intended to have the same meaning as commonly understood by one of ordinary skill in the art. Unless otherwise indicated, such as through context, as used herein, the following terms are intended to have the following meanings:

As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

Embodiments of the present disclosure provide imaging devices that are insertable into a subject or patient for imaging internal tissues, and methods of use thereof. Some embodiments of the present disclosure relate to minimally invasive medical procedures that are performed via an access port, whereby surgery, diagnostic imaging, therapy, or other medical procedures (e.g. minimally invasive medical procedures) are performed based on access to internal tissue through the access port.

Figure 2:
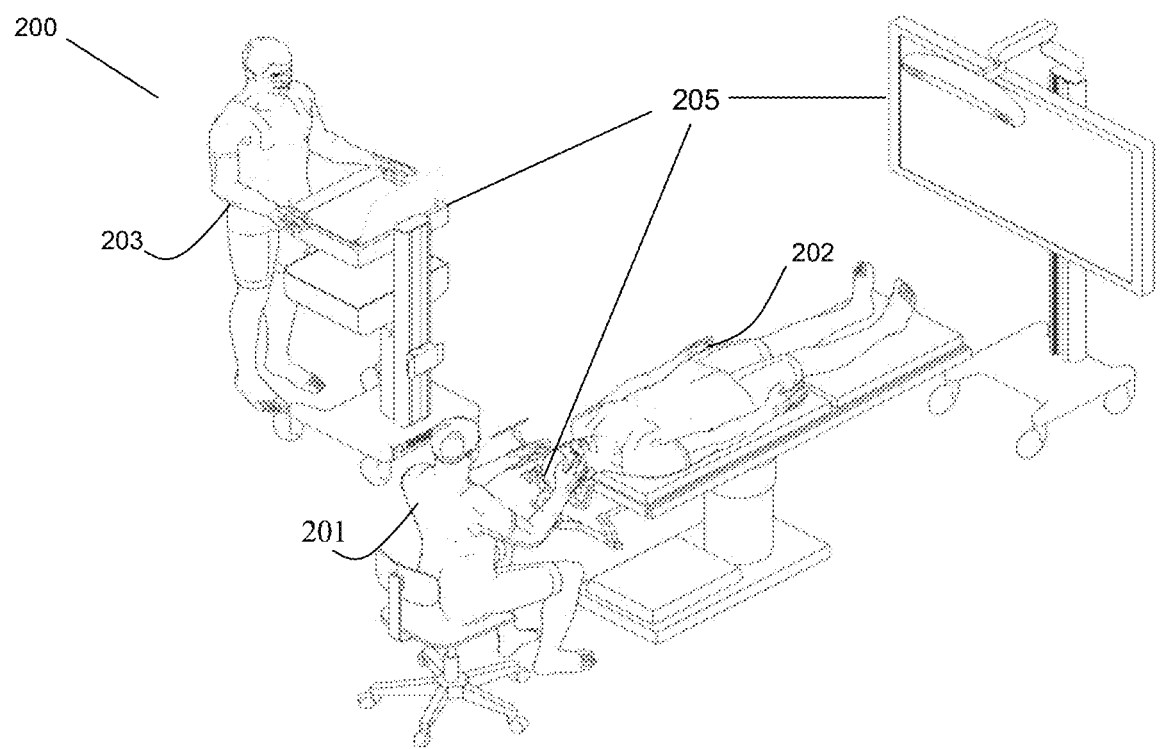
FIG. 2 shows an exemplary navigation system to support minimally invasive access port-based surgery.

Referring to FIG. 2, an exemplary navigation system environment 200 is shown, which may be used to support navigated image-guided surgery. As shown in FIG. 2, surgeon 201 conducts a surgery on a patient 202 in an operating room (OR) environment. A medical navigation system 205 comprising an equipment tower, tracking system, displays and tracked instruments assist the surgeon 201 during his procedure. An operator 203 is also present to operate, control and provide assistance for the medical navigation system 205.

Figure 3:
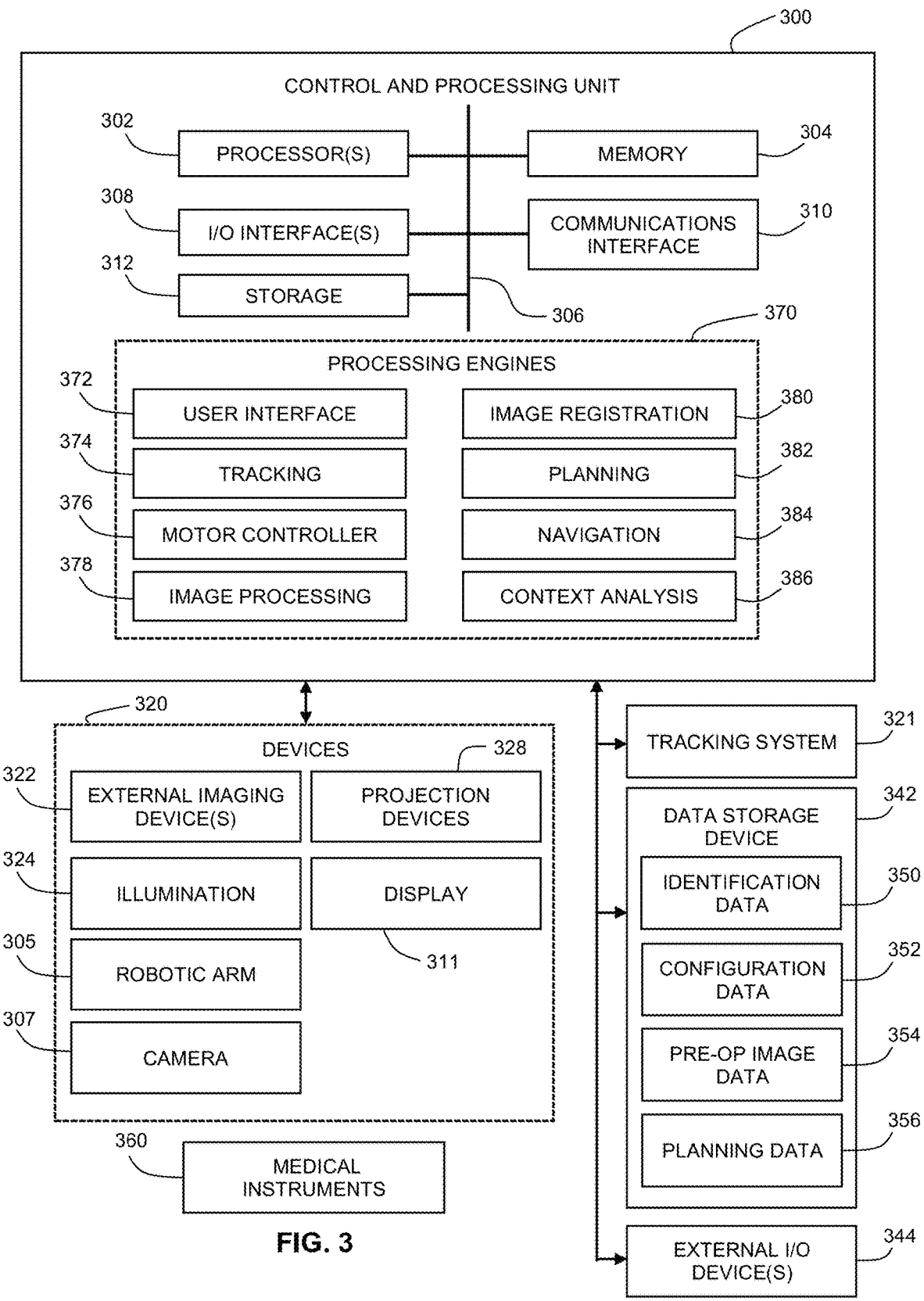
FIG. 3 is a block diagram illustrating a control and processing system that may be used in the navigation system shown in FIG. 2.

Referring to FIG. 3, a block diagram is shown illustrating a control and processing system 300 that may be used in the medical navigation system 200 shown in FIG. 3 (e.g., as part of the equipment tower). As shown in FIG. 3, in one example, control and processing system 300 may include one or more processors 302, a memory 304, a system bus 306, one or more input/output interfaces 308, a communications interface 310, and storage device 312. Control and processing system 300 may be interfaced with other external devices, such as tracking system 321, data storage 342, and external user input and output devices 344, which may include, for example, one or more of a display, keyboard, mouse, sensors attached to medical equipment, foot pedal, and microphone and speaker. Data storage 342 may be any suitable data storage device, such as a local or remote computing device (e.g. a computer, hard drive, digital media device, or server) having a database stored thereon. In the example shown in FIG. 3, data storage device 342 includes identification data 350 for identifying one or more medical instruments 360 and configuration data 352 that associates customized configuration parameters with one or more medical instruments 360. Data storage device 342 may also include preoperative image data 354 and/or medical procedure planning data 356. Although data storage device 342 is shown as a single device in FIG. 3, it will be understood that in other embodiments, data storage device 342 may be provided as multiple storage devices.

Medical instruments 360 are identifiable by control and processing unit 300. Medical instruments 360 may be connected to and controlled by control and processing unit 300, or medical instruments 360 may be operated or otherwise employed independent of control and processing unit 300. Tracking system 321 may be employed to track one or more of medical instruments 360 and spatially register the one or more tracked medical instruments to an intraoperative reference frame. For example, medical instruments 360 may include tracking markers such as tracking spheres that may be recognizable by a tracking camera 307. In one example, the tracking camera 307 may be an infrared (IR) tracking camera. In another example, as sheath placed over a medical instrument 360 may be connected to and controlled by control and processing unit 300.

Control and processing unit 300 may also interface with a number of configurable devices, and may intraoperatively reconfigure one or more of such devices based on configuration parameters obtained from configuration data 352. Examples of devices 320, as shown in FIG. 3, include one or more external imaging devices 322, one or more illumination devices 324, a robotic arm 305, one or more projection devices 328, and one or more displays 205, 211.

Exemplary aspects of the disclosure can be implemented via processor(s) 302 and/or memory 304. For example, the functionalities described herein can be partially implemented via hardware logic in processor 302 and partially using the instructions stored in memory 304, as one or more processing modules or engines 370. Example processing modules include, but are not limited to, user interface engine 372, tracking module 374, motor controller 376, image processing engine 378, image registration engine 380, procedure planning engine 382, navigation engine 384, and context analysis module 386. While the example processing modules are shown separately in FIG. 3, in one example the processing modules 370 may be stored in the memory 304 and the processing modules may be collectively referred to as processing modules 370.

It is to be understood that the system is not intended to be limited to the components shown in FIG. 3. One or more components of the control and processing system 300 may be provided as an external component or device. In one example, navigation module 384 may be provided as an external navigation system that is integrated with control and processing system 300.

Some embodiments may be implemented using processor 302 without additional instructions stored in memory 304. Some embodiments may be implemented using the instructions stored in memory 304 for execution by one or more general purpose microprocessors. Thus, the disclosure is not limited to a specific configuration of hardware and/or software.

While some embodiments can be implemented in fully functioning computers and computer systems, various embodiments are capable of being distributed as a computing product in a variety of forms and are capable of being applied regardless of the particular type of machine or computer readable media used to actually effect the distribution.

At least some aspects disclosed can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache or a remote storage device.

A computer readable storage medium can be used to store software and data which, when executed by a data processing system, causes the system to perform various methods. The executable software and data may be stored in various places including for example ROM, volatile RAM, nonvolatile memory and/or cache. Portions of this software and/or data may be stored in any one of these storage devices.

Examples of computer-readable storage media include, but are not limited to, recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions may be embodied in digital and analog communication links for electrical, optical, acoustical or other forms of propagated signals, such as carrier waves, infrared signals, digital signals, and the like. The storage medium may be the internet cloud, or a computer readable storage medium such as a disc.

At least some of the methods described herein are capable of being distributed in a computer program product comprising a computer readable medium that bears computer usable instructions for execution by one or more processors, to perform aspects of the methods described. The medium may be provided in various forms such as, but not limited to, one or more diskettes, compact disks, tapes, chips, USB keys, external hard drives, wire-line transmissions, satellite transmissions, internet transmissions or downloads, magnetic and electronic storage media, digital and analog signals, and the like. The computer useable instructions may also be in various forms, including compiled and non-compiled code.

According to one aspect of the present application, one purpose of the navigation system 205, which may include control and processing unit 300, is to provide tools to the neurosurgeon that will lead to the most informed, least damaging neurosurgical operations. In addition to removal of brain tumours and intracranial hemorrhages (ICH), the navigation system 205 can also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, aspects of the present disclosure may be applied to any suitable medical procedure.

Figure 4A:
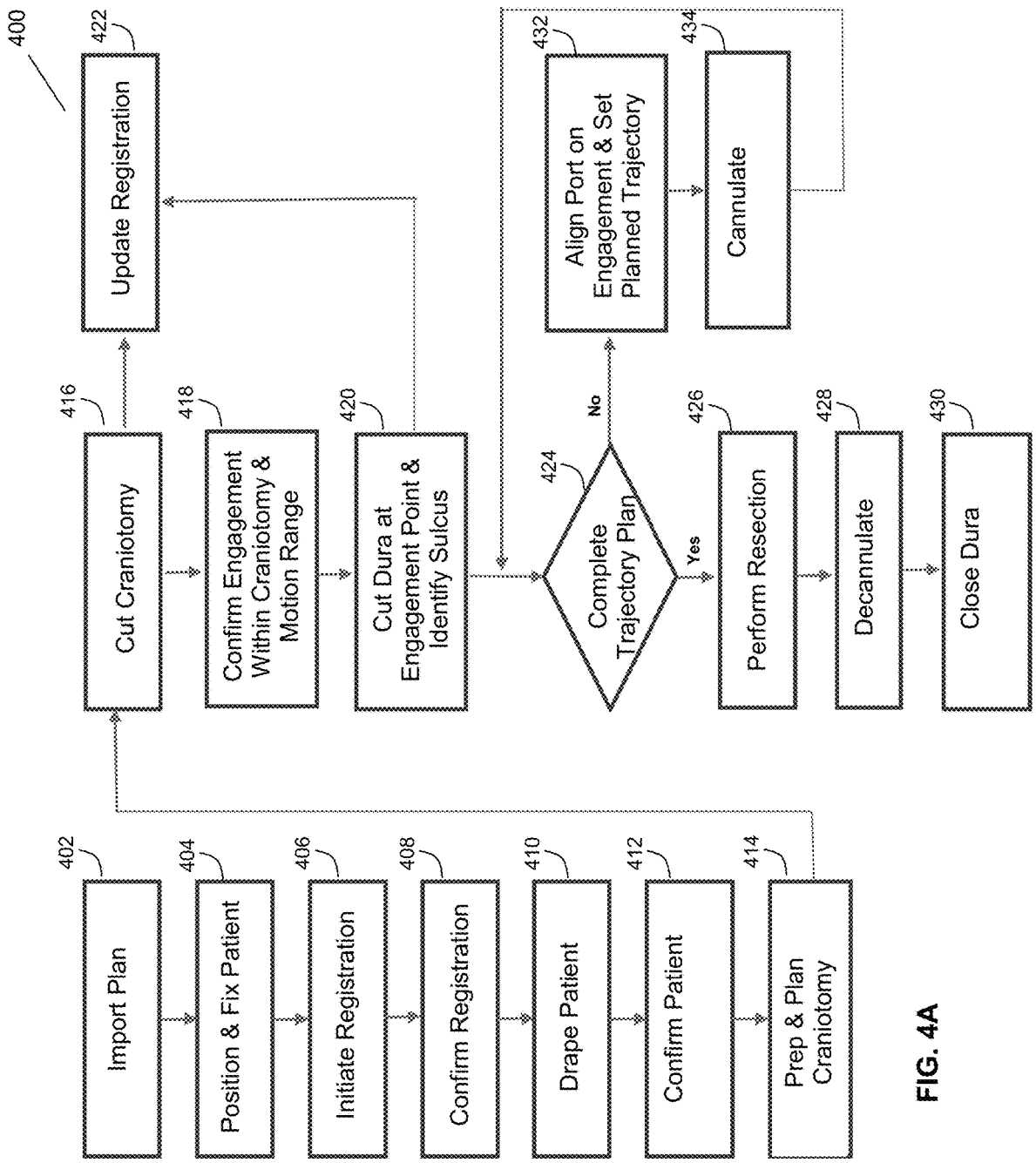
FIG. 4A is a flow chart illustrating a method involved in a surgical procedure using the navigation system of FIG. 2.

Referring to FIG. 4A, a flow chart is shown illustrating a method 400 of performing a port-based surgical procedure using a navigation system, such as the medical navigation system 200 described in relation to FIG. 2. At a first block 402, the port-based surgical plan is imported.

Once the plan has been imported into the navigation system at the block 402, the patient is affixed into position using a body holding mechanism. The head position is also confirmed with the patient plan in the navigation system (block 404), which in one example may be implemented by the computer or controller forming part of the equipment tower 201.

Next, registration of the patient is initiated (block 406). The phrase "registration" or "image registration" refers to the process of transforming different sets of data into one coordinate system. Data may include multiple photographs, data from different sensors, times, depths, or viewpoints. The process of "registration" is used in the present application for medical imaging in which images from different imaging modalities are co-registered. Registration is used in order to be able to compare or integrate the data obtained from these different modalities.

Those skilled in the relevant arts will appreciate that there are numerous registration techniques available and one or more of the techniques may be applied to the present example. Non-limiting examples include intensity-based methods that compare intensity patterns in images via correlation metrics, while feature-based methods find correspondence between image features such as points, lines, and contours. Image registration methods may also be classified according to the transformation models they use to relate the target image space to the reference image space. Another classification can be made between single-modality and multi-modality methods. Single-modality methods typically register images in the same modality acquired by the same scanner or sensor type, for example, a series of magnetic resonance (MR) images may be co-registered, while multi-modality registration methods are used to register images acquired by different scanner or sensor types, for example in magnetic resonance imaging (MRI) and positron emission tomography (PET). In the present disclosure, multi-modality registration methods may be used in medical imaging of the head and/or brain as images of a subject are frequently obtained from different scanners. Examples include registration of brain computerized tomography (CT)/MRI images or PET/CT images for tumor localization, registration of contrast-enhanced CT images against non-contrast-enhanced CT images, and registration of ultrasound and CT.

Figure 4B:
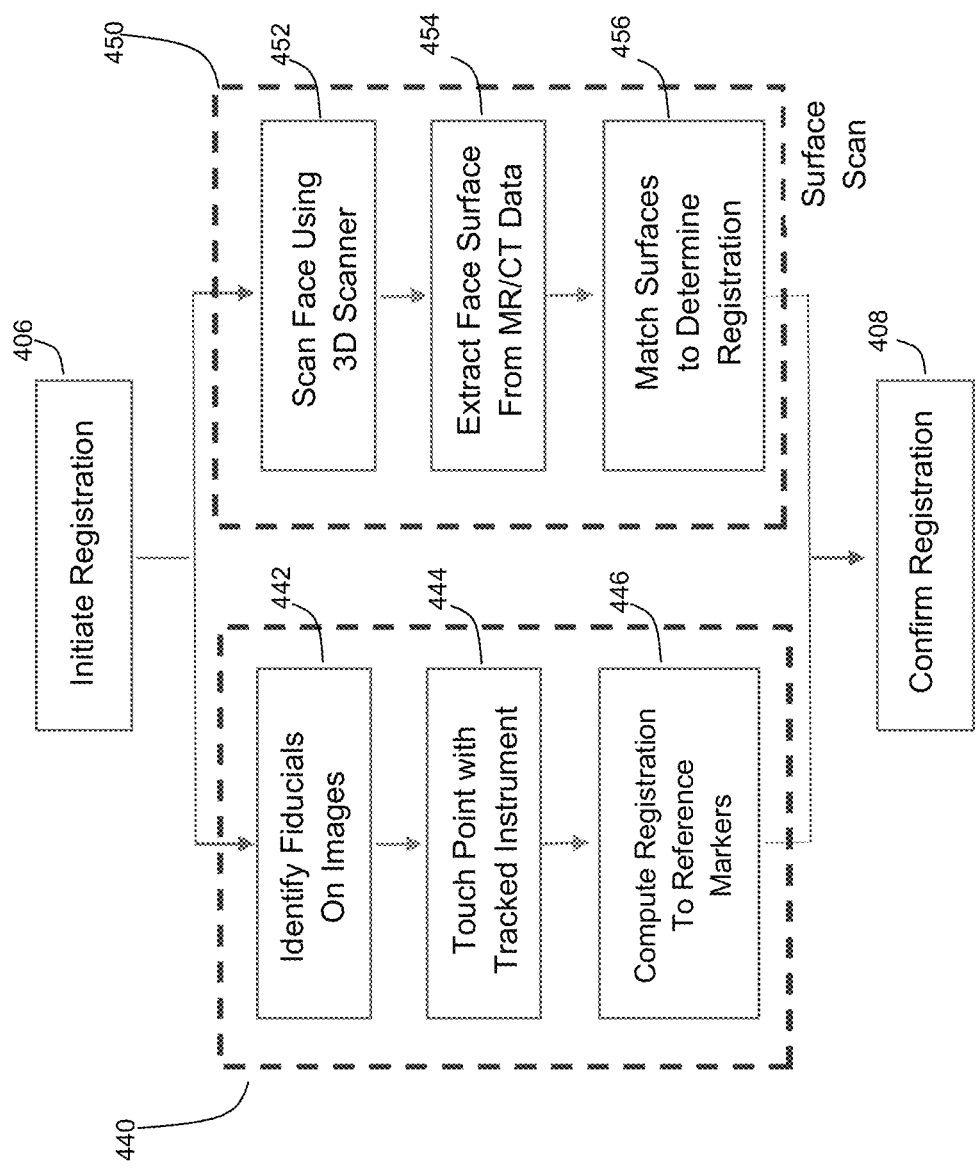
FIG. 4B is a flow chart illustrating a method of registering a patient for a surgical procedure as outlined in FIG. 4A.

Referring now to FIG. 4B, a flow chart is shown illustrating a method involved in registration block 406 as outlined in FIG. 4A, in greater detail. If the use of fiducial touch points (440) is contemplated, the method involves first identifying fiducials on images (block 442), then touching the touch points with a tracked instrument (block 444). Next, the navigation system computes the registration to reference markers (block 446).

Alternately, registration can also be completed by conducting a surface scan procedure (block 450). The block 450 is presented to show an alternative approach, but may not typically be used when using a fiducial pointer. First, the face is scanned using a 3D scanner (block 452). Next, the face surface is extracted from MR/CT data (block 454). Finally, surfaces are matched to determine registration data points (block 456).

Upon completion of either the fiducial touch points (440) or surface scan (450) procedures, the data extracted is computed and used to confirm registration at block 408, shown in FIG. 4A.

Referring back to FIG. 4A, once registration is confirmed (block 408), the patient is draped (block 410). Typically, draping involves covering the patient and surrounding areas with a sterile barrier to create and maintain a sterile field during the surgical procedure. The purpose of draping is to eliminate the passage of microorganisms (e.g., bacteria) between non-sterile and sterile areas. At this point, conventional navigation systems require that the non-sterile patient reference is replaced with a sterile patient reference of identical geometry location and orientation.

Upon completion of draping (block 410), the patient engagement points are confirmed (block 412) and then the craniotomy is prepared and planned (block 414).

Upon completion of the preparation and planning of the craniotomy (block 414), the craniotomy is cut and a bone flap is temporarily removed from the skull to access the brain (block 416). Registration data is updated with the navigation system at this point (block 422).

Next, the engagement within craniotomy and the motion range are confirmed (block 418). Next, the procedure advances to cutting the dura at the engagement points and identifying the sulcus (block 420).

Thereafter, the cannulation process is initiated (block 424). Cannulation involves inserting a port into the brain, typically along a sulci path as identified at 420, along a trajectory plan. Cannulation is typically an iterative process that involves repeating the steps of aligning the port on engagement and setting the planned trajectory (block 432) and then cannulating to the target depth (block 434) until the complete trajectory plan is executed (block 424).

Once cannulation is complete, the surgeon then performs resection (block 426) to remove part of the brain and/or tumor of interest. The surgeon then decannulates (block 428) by removing the port and any tracking instruments from the brain. Finally, the surgeon closes the dura and completes the craniotomy (block 430). Some aspects of FIG. 4A are specific to port-based surgery, such as portions of blocks 428, 420, and 434, but the appropriate portions of these blocks may be skipped or suitably modified when performing non-port based surgery.

When performing a surgical procedure using a medical navigation system 200, as outlined in connection with FIGS. 4A and 4B, the medical navigation system 200 must acquire and maintain a reference of the location of the tools in use as well as the patient in three dimensional (3D) space. In other words, during a navigated neurosurgery, there needs to be a tracked reference frame that is fixed relative to the patient's skull. During the registration phase of a navigated neurosurgery (e.g., the step 406 shown in FIGS. 4A and 4B), a transformation is calculated that maps the frame of reference of preoperative MRI or CT imagery to the physical space of the surgery, specifically the patient's head. This may be accomplished by the navigation system 200 tracking locations of fiducial markers fixed to the patient's head, relative to the static patient reference frame. The patient reference frame is typically rigidly attached to the head fixation device, such as a Mayfield clamp. Registration is typically performed before the sterile field has been established (e.g., the step 410 shown in FIG. 4A).

Figure 5:
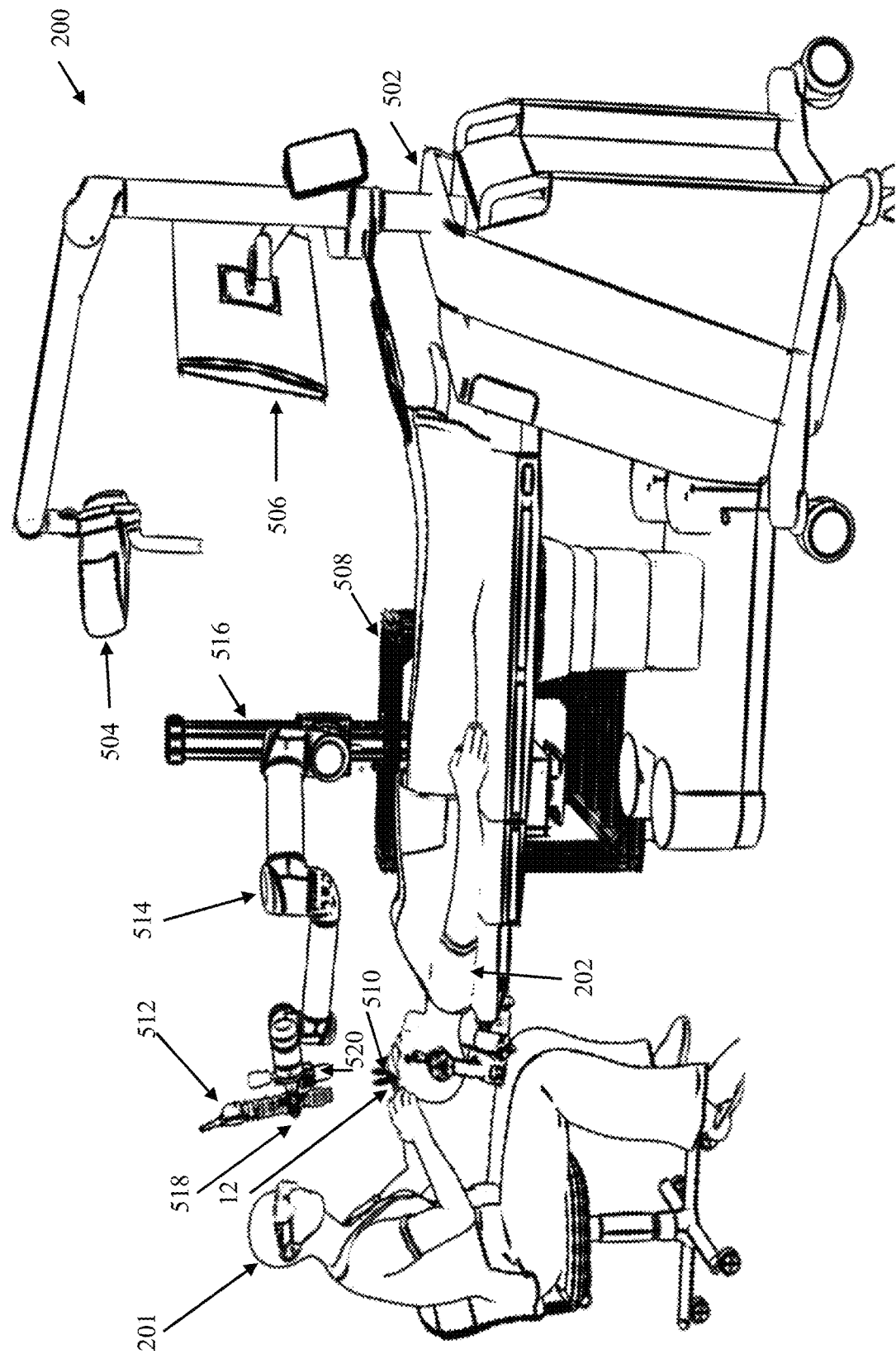
FIG. 5 is an exemplary navigation system similar to FIG. 2 illustrating system components of an exemplary surgical system used in port based surgery.

FIG. 5 is a diagram illustrating components of an exemplary surgical system used in port based surgery that is similar to FIG. 2. FIG. 5 illustrates a navigation system 200 having an equipment tower 502, tracking system 504, display 506, an intelligent positioning system 508 and tracking markers 510 used to tracked instruments or an access port 12. Tracking system 504 may also be considered an optical tracking device or tracking camera. In FIG. 5, a surgeon 201 is performing a tumor resection through a port 12, using an imaging device 512 to view down the port at a suffcient magnification to enable enhanced visibility of the instruments and tissue. The imaging device 512 may be an external scope, videoscope, wide field camera, or an alternate image capturing device. The imaging sensor view is depicted on the visual display 506 which surgeon 201 uses for navigating the port's distal end through the anatomical region of interest.

An intelligent positioning system 508 comprising an automated arm 514, a lifting column 516 and an end effector 518, is placed in proximity to patient 202. Lifting column 516 is connected to a frame of intelligent positioning system 508. As seen in FIG. 5, the proximal end of automated mechanical arm 514 (further known as automated arm herein) is connected to lifting column 516. In other embodiments, automated arm 514 may be connected to a horizontal beam, which is then either connected to lifting column 516 or directly to frame of the intelligent positioning system 508. Automated arm 514 may have multiple joints to enable 5, 6 or 7 degrees of freedom.

End effector 518 is attached to the distal end of automated arm 514. End effector 518 may accommodate a plurality of instruments or tools that may assist surgeon 201 in his procedure. End effector 518 is shown as holding an external scope, however it should be noted that this is merely an example and alternate devices may be used with the end effector 518 such as a wide field camera, microscope and OCT (Optical Coherence Tomography) or other imaging instruments. In another example, multiple end effectors may be attached to the distal end of automated arm 518, and thus assist the surgeon 201 in switching between multiple modalities. For example, the surgeon 201 may want the ability to move between microscope, and OCT with stand-off optics. In a further example, the ability to attach a second, more accurate, but smaller range end effector such as a laser based ablation system with micro-control may be contemplated.

The intelligent positioning system 508 receives as input the spatial position and pose data of the automated arm 514 and target (for example the port 12) as determined by tracking system 504 by detection of the tracking markers on the wide field camera on port 12. Further, it should be noted that the tracking markers may be used to track both the automated arm 514 as well as the end effector 518 either collectively or independently. It should be noted that a wide field camera 520 is shown in this image and that it is connected to the external scope (e.g., imaging device 512) and the two imaging devices together are held by the end effector 518. It should additionally be noted that although these are depicted together for illustration of the diagram that either could be utilized independently of the other, for example where an external video scope can be used independently of the wide field camera 520.

Intelligent positioninng system 508 computes the desired joint positions for automated arm 514 so as to maneuver the end effector 518 mounted on the automated arm's distal end to a predetermined spatial positoin and pose relative to the port 12. This redetermined relative spatial position and pose is termed the "Zero Position" where the sensor of imaging device 512 and port 12 are axially alligned.

Further, the intelligent positioning system 508, optical tracking device 504, automated arm 514, and tracking markers 510 form a feedback loop. This feedback loop works to keep the distal end of the port 12 (located inside the brain) in constant view and focus of the end effector 518 given that it is an imaging device as the port position may be dynamically manipulated by the surgeon during the procedure. Intelligent positioning system 508 may also include a foot pedal for use by the surgeon 201 to align the end effector 518 (i.e., holding a videoscope) of automated arm 514 with the port 12.

Figure 6:
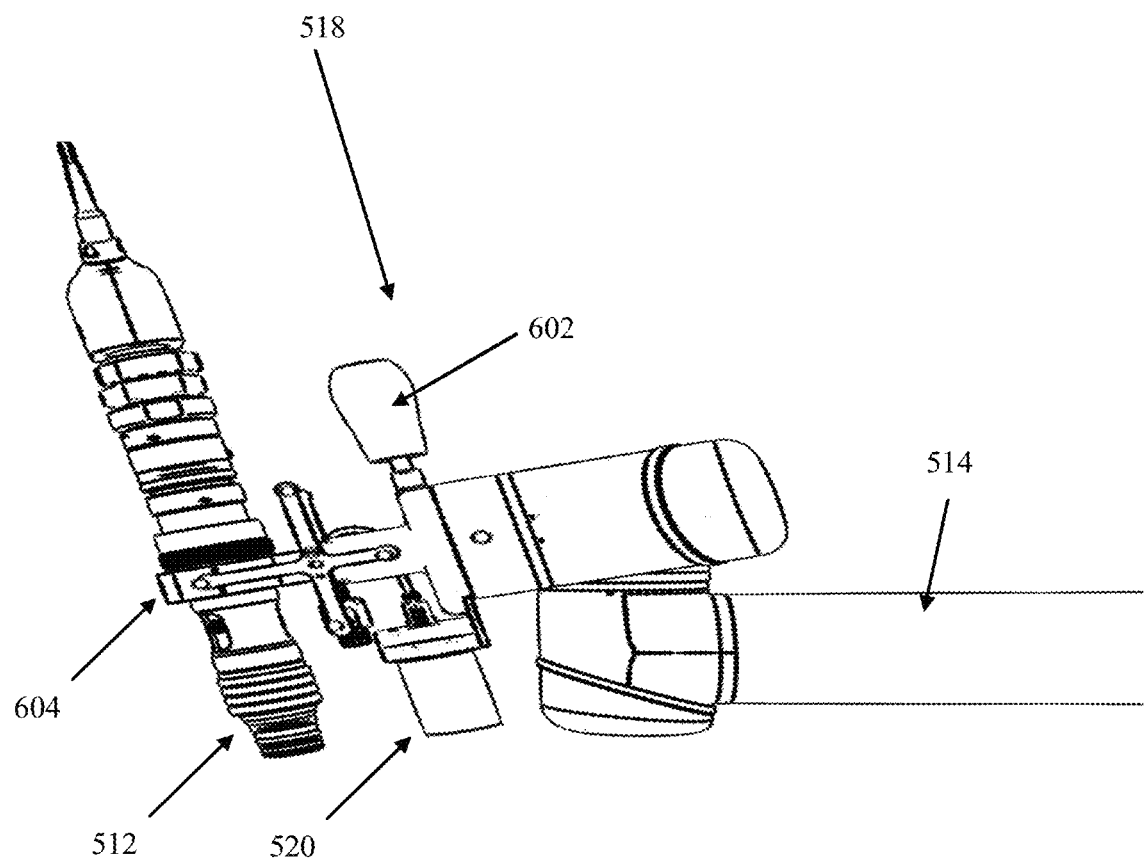
FIG. 6 is perspective drawing illustrating a conventional end effector holding a camera.

Referring to FIG. 6, a conventional end effector 518 is shown attached to automated arm 514. The end effector 518 includes a handle 602 and a scope clamp 604. The scope clamp 604 holds imaging device 512. The end effector also has wide field camera 520 attached thereto.

Figure 7:
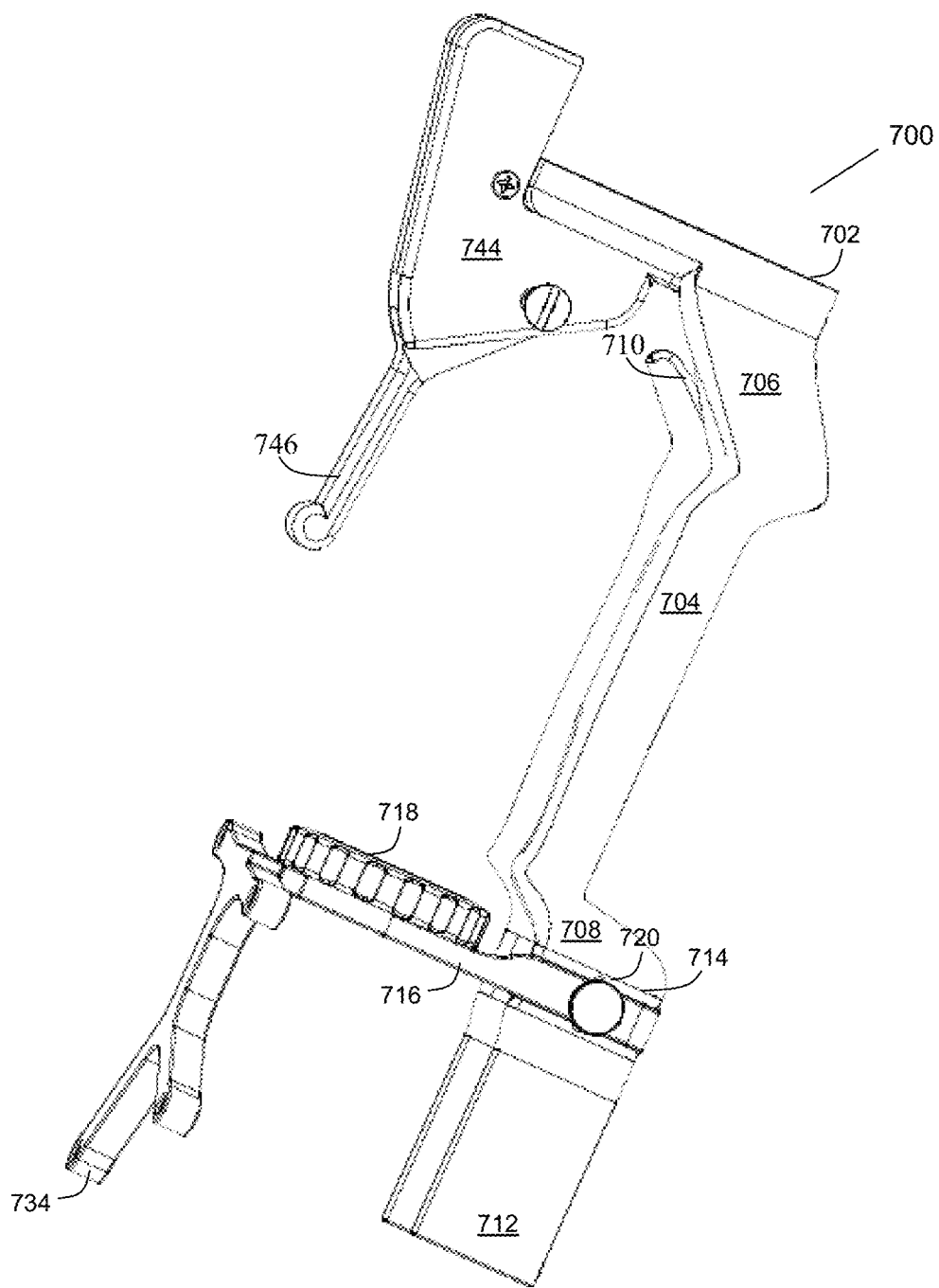
FIG. 7 is a perspective drawing illustrating an end effector according to aspects of the present description.
Figure 8:
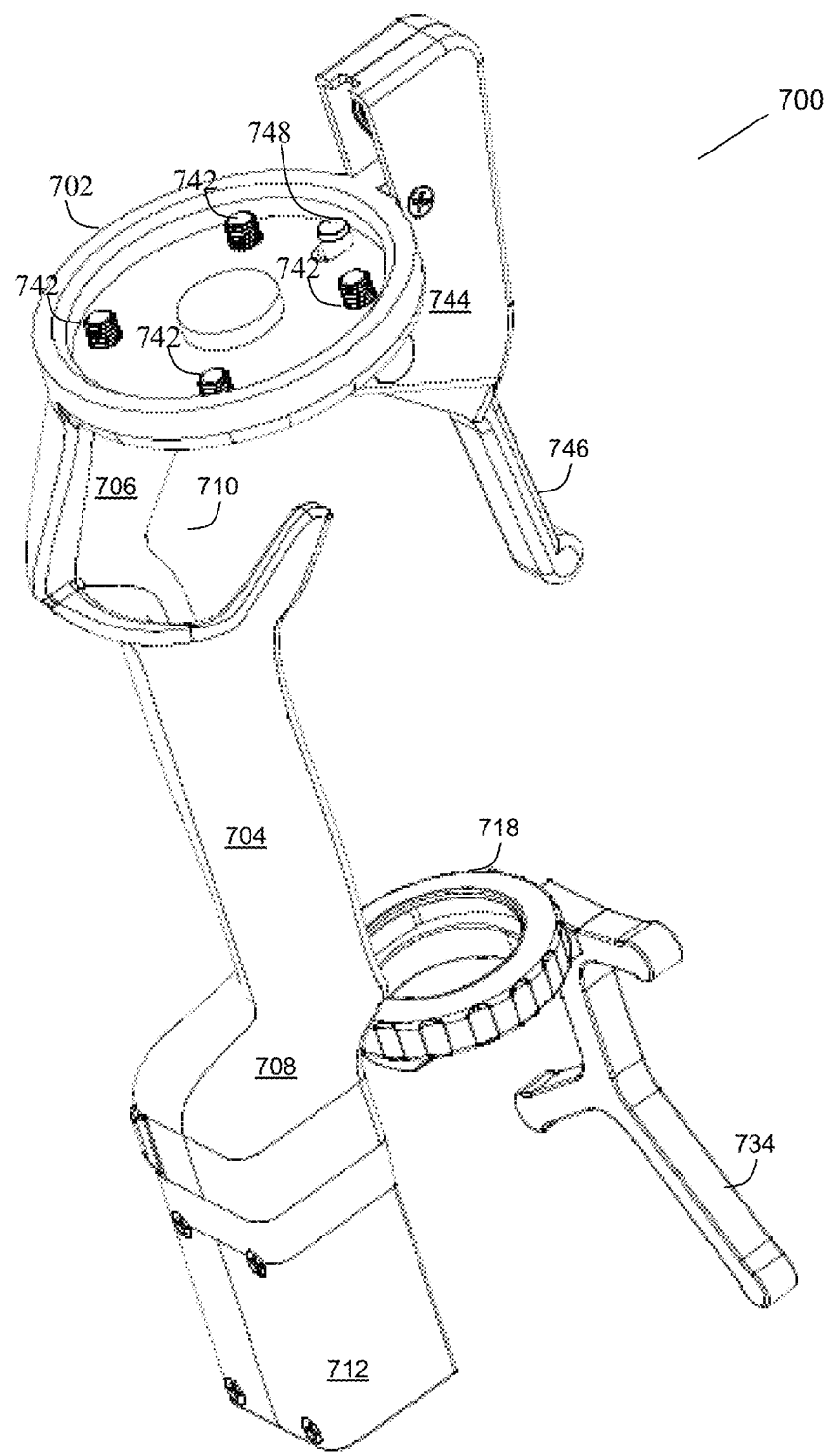
FIG. 8 is another perspective drawing showing the end effector of FIG. 7.
Figure 9:
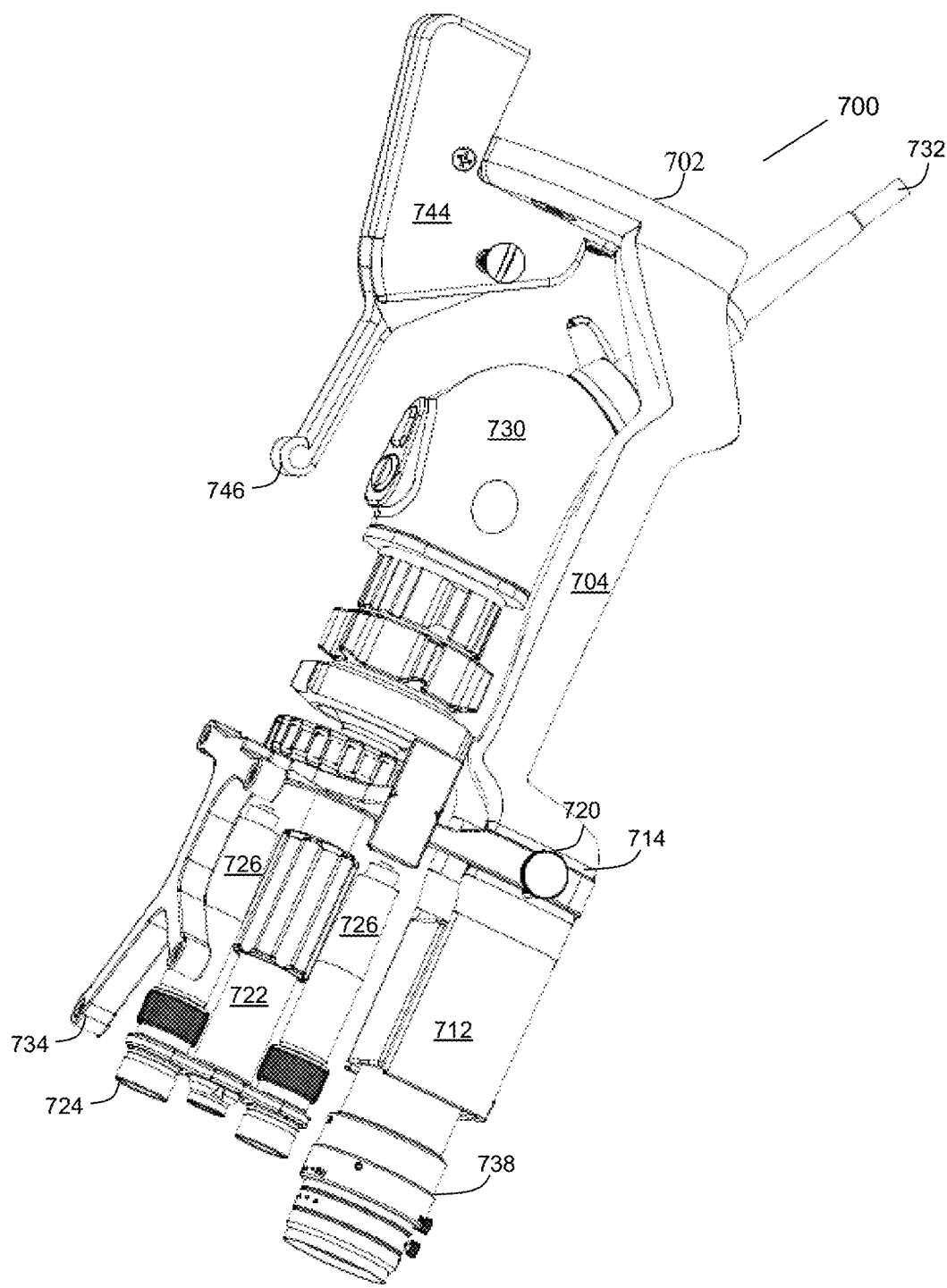
FIG. 9 is another perspective drawing showing the end effector of FIG. 7 holding a camera and a videoscope.
Figure 10:
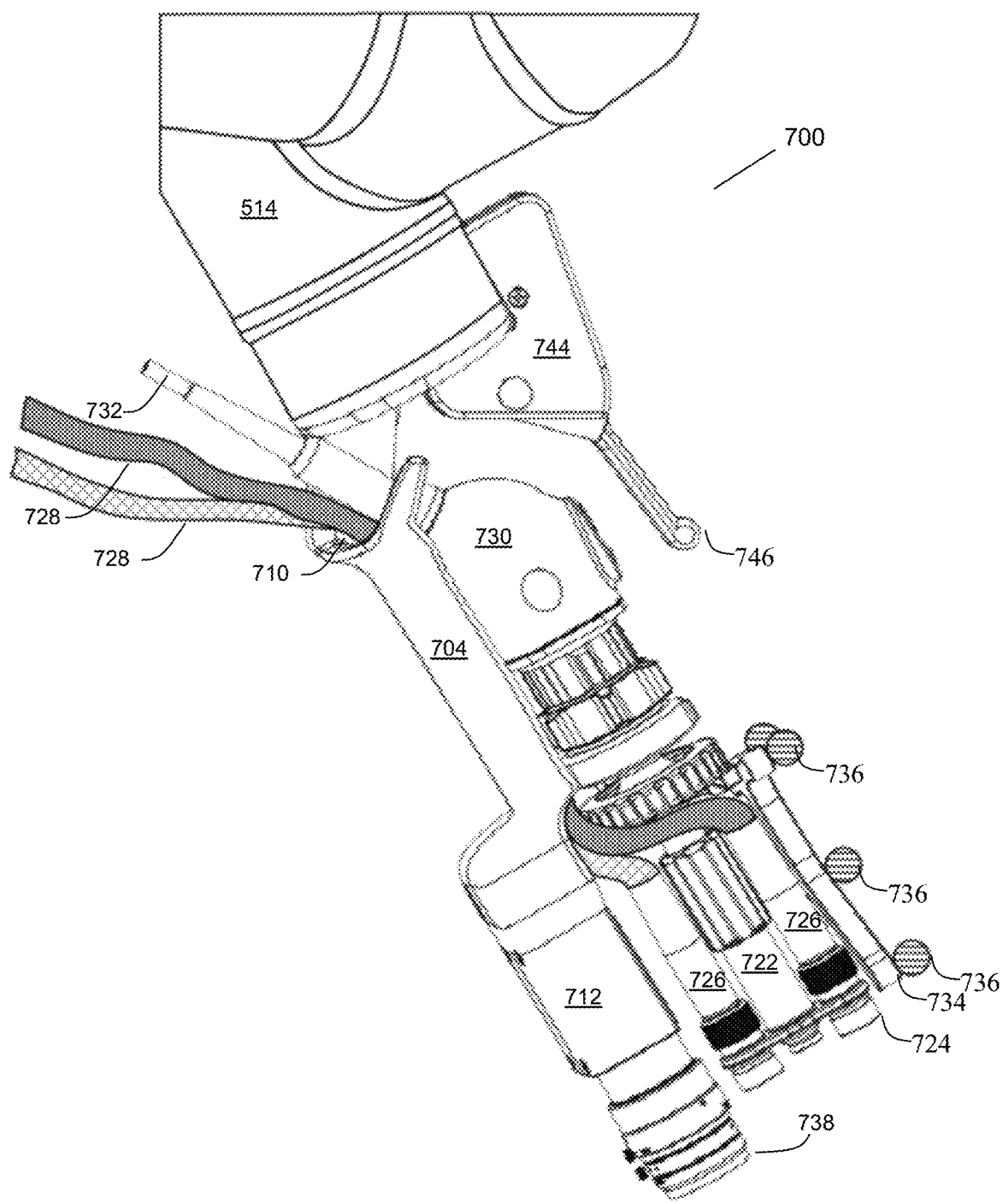
FIG. 10 is another perspective drawing showing the end effector of FIG. 7 holding a camera and a videoscope and connected to an automated arm of a positioning device.

Referring now to FIG. 7, a perspective drawing is shown illustrating an end effector 700 according to aspects of the present description. FIG. 8 is another perspective drawing showing the end effector 700 of FIG. 7 from a different viewpoint. FIG. 9 is another perspective drawing showing the end effector 700 of FIG. 7 holding a scope and camera. FIG. 10 is another perspective drawing from a different perspective showing the end effector 700 of FIG. 9 holding the scope and camera and connected to a positioning arm of a positioning device. FIGS. 7-10 will now be discussed concurrently.

The end effector 700 may connect to a positioning arm, such as the automated arm 514 of a medical navigation system 200. The end effector 700 has a mating component 702 for connecting to an output flange of the positioning arm. The end effector 700 further has a handle portion 704 having a first end 706 and a second end 708. The first end 706 extends from the mating component 702. The handle portion 704 includes a cable cut-out 710 at the first end 706 for receiving and managing cables. A camera mount 712 is connected to the second end 708 of the handle portion 704.

The end effector 700 further has a mechanical interface 714 located at the second end 708 of the handle portion 704. A scope clamp arm 716 may be connected to the mechanical interface 714. The scope clamp arm 716 may have a fastening ring 718 for securing a scope, such as a videoscope. In one example, the mechanical interface 714 may include a dovetail interface with the scope clamp arm 716 slideably engaged therein and secured by a screw 720. In one example, the screw 720 may be a thumbscrew for easily attaching and detaching the scope clamp arm 716. The scope clamp arm 716 may be connectable to a scope 722 (FIGS. 9 and 10) for clamping the scope 722 in position adjacent the camera mount 712 using the fastening ring 718. The scope 722 may further have an illuminator 724 (FIGS. 9 and 10) at a distal end of the scope 722 that is connectable to at least one light pipe 726 (FIGS. 9 and 10). In one example, two light pipes 726 may be used. The light pipes 726 may have cables 728 (FIGS. 9 and 10) leading thereto. In one example, the cables 728 may be fiber optic cables that conduct electromagnetic energy in the visible spectrum.

In one example, the scope 722 may be an exoscope and a camera 730 is mountable on a proximal end of the exoscope. In one example, the camera 730 may be a surgical site camera for displaying a magnified image of a surgical site. One or more cables 732 leading to the camera 730 and the cables 728 leading to at least one light pipe may be positioned through the cable cut-out 710, therefore managing the cables in the vicinity of the end effector 700 and avoid clutter in the workspace of the surgeon.

The scope clamp arm 716 may further having a tracking marker frame 734 attached thereto. The tracking marker frame 734 has a coupling for connecting to a tracking marker 736 (FIG. 10). The tracking marker may be any of passive reflective tracking spheres, active infrared (IR) markers, active light emitting diodes (LEDs), or a graphical pattern. In one example, there are at least three couplings on the frame 734 connected to at least three respective tracking markers 736. In one example, there may be four passive reflective tracking spheres coupled to the frame 734. While some specific examples of the type and number of tracking markers 736 have been given, any suitable tracking marker type and configuration may be used to meet the design criteria of a particular application.

In one example, the camera mount 712 connected to the second end 708 of the handle portion 704 has a camera 738 (FIGS. 9 and 10) mounted thereon. The camera 738 may also have a cable (not shown) connected to the camera 738 that may also extend through the cable cut-out 710. In one example, the camera 738 may be a situational awareness camera that shows a macroscopic view of the medical or surgical workspace on a display, such as a display 506, such that the surgeon can see what is going on in the vicinity of the surgical area of interest without having to divert his or her eyes from the display (or displays) 506 where the magnified view of the surgical area of interest from the camera 730 is being displayed.

In one example, the mating component 702 connects to the output flange of the positioning arm with a dowel pin 748 (FIG. 8) for localization and is mechanically secured with at least one screw 742. In one example, the positioning arm 514 may use a standard ISO 9409-1-50-4-M6 tool output flange. The flange and a dowel pin 748 may be used for localization, while four M6 screws may secure the mating component 702 to the positioning arm. In one example, the mating component may also include an 8-pin M8 connector to a Lumberg RSMEDG8 connector on the positioning arm. While a specific example is provided of how the mating component 702 may connect to the positioning arm 514 both mechanically and electrically, any suitable connection may be used to meet the design criteria of a particular application.

The end effector 700 may further have a trigger mechanism 744 located adjacent the mating component 702 for mechanically communicating with the positioning arm. A trigger 746 may emanate from the trigger mechanism 744. Actuation of the trigger 746 may place the positioning arm 514 into compliant mode providing for manual positioning of the positioning arm 514 using the handle portion 704. In one example, the trigger mechanism 744 may include a switch that communicates electrically with the control and processing unit 300.

In one example, the end effector 700 may be designed to be as thin as possible so that the end effector does not obstruct the view of a surgeon using the end effector 700. In one example, the trigger mechanism 744, the handle 704, the first camera 730, the second camera 738, the scope 722, the scope clamp arm 716, and the tracking marker frame 734 all have respective center lines that are substantially aligned resulting in a thin profile that reduces obstruction of the view of a surgeon using the end effector 700 in the medical navigation system 200.

The end effector 700 may also have a force-moment sensor (not shown), which in one example could be positioned between the end-effector 700 and the positioning arm 514. In one example, the force-moment sensor could be cylindrical, similar to the mating component, and may form part of the end-effector (e.g., may be positioned just above the mating component 702). The force-moment sensor may provide for a force-moment accommodation (FMA) mode, where the controller receives a signal from the force moment sensor and moves the positioning arm in response to forces applied to the end effector 700 and sensed by the force-moment sensor.

In one example, the positioning arm 514 and the end effector 700 including the mating component 702 and the handle portion 704 are draped, whereas the scope 722, the illuminator 724, the fastening ring 718, and the tracking marker frame 734 are made of a material that is sterilizable and will not be draped. The scope clamp arm 716 may protrude from the drape and also be made of a sterilizable material.

The end effector 700 may aim to meet a number of objectives, including holding the exoscope 722, providing the trigger 746 and trigger mechanism 744 to place the positioning arm 514 into manual positioning mode when the trigger 746 is depressed, allowing for easy access to any buttons on the camera 730 when using the end effector 700, allowing for the scope 722 to be quickly and easily replaced, providing a handle 704 to handle the positioning arm 514 to which the end effector 700 is attached, keeping the light pipes 726 and all cables 728, 732 neatly managed and out of the workspace of the surgeon and away from the handle 704, providing for appropriate placement of tracking markers 736 within field of view of the tracking camera 504, maintaining the scope 722, cameras 730, 738, and tracking markers 736 outside of the sterile drape so that the drape does not interfere with optics while the remaining components may be draped, and maintaining a clear line of site to the display 506.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

The invention claimed is:

1. An end effector for connecting to a multi-jointed robotic arm of a positioning device of a medical navigation system, the end effector comprising:
a mating component for connecting to an output flange at a distal end of the multi-jointed robotic arm;
a handle portion having a first end and a second end, the first end extending from the mating component, the handle portion including a cable cut-out at the first end;
a camera mount connected to the second end of the handle portion;
a trigger mechanism located adjacent the mating component for communicating with the multi-jointed robotic arm; and
a trigger emanating from the trigger mechanism, at least one of the trigger or trigger mechanism being configured to be manually held, the trigger being configured to be manually actuated; and
a scope clamp arm connected to the mechanical interface for clamping a scope, the scope clamp arm having a tracking marker frame attached thereto, the tracking marker frame having at least three couplings on the frame connected to at least three respective tracking markers, the tracking markers being passive reflective tracking spheres;
wherein manual actuation of the trigger places the multi-jointed robotic arm into compliant mode in which manual positioning of the joints of the multi-jointed robotic arm is enabled, wherein manual positioning of the joints is facilitated using the handle portion to directly and physically manually manipulate the end effector and the multi-jointed robotic arm to which the end effector is connected.

2. The end effector according to claim 1, further comprising:
a mechanical interface located at the second end of the handle portion.

3. The end effector according to claim 2, wherein the mechanical interface includes a dovetail interface with the scope clamp arm engaged therein and secured by a screw.

4. The end effector according to claim 1, wherein the camera mount connected to the second end of the handle portion has a second camera mounted thereon, with a cable connected to the second camera extending through the cable cut-out.

5. The end effector according to claim 4, wherein the second camera includes a situational awareness camera.

6. The end effector according to claim 5, wherein the mating component connects to the output flange with a dowel pin and is secured with at least one screw.

7. The end effector according to claim 6, wherein the trigger mechanism, the handle, a first camera, the second camera, the scope, the scope clamp arm, and the tracking marker frame all have respective center lines that are substantially aligned resulting in a thin profile that reduces visual_obstruction of a surgeon using the end effector in the medical navigation system.

8. A medical navigation system, comprising:
a positioning device having a multi-jointed robotic arm with an output flange at a distal end of the multi-jointed robotic arm;
a controller at least electrically coupled to the positioning device, the controller having a processor coupled to a memory and a display; and
an end effector connected to the distal end of the multi-jointed robotic arm of the positioning device, the end effector comprising:
a mating component connected to the output flange;
a handle portion having a first end and a second end, the first end extending from the mating component, the handle portion including a cable cut-out at the first end;
a camera mount connected to the second end of the handle portion;
a trigger mechanism located adjacent the mating component for communicating with the multi-jointed robotic arm; and a trigger emanating from the trigger mechanism, at least one of the trigger or trigger mechanism being configured to be manually held, the trigger being configured to be manually actuated; and a scope clamp arm connected to the mechanical interface for clamping a scope, the scope clamp arm having a tracking marker frame attached thereto, the tracking marker frame having at least three couplings on the frame connected to at least three respective tracking markers, the tracking markers being passive reflective tracking spheres;

wherein manual actuation of the trigger places the multi-jointed robotic arm into compliant mode in which manual positioning of the joints of the multi-jointed robotic arm is enabled, wherein manual positioning of the joints is facilitated using the handle portion to directly and physically manually manipulate the end effector and the multi-jointed robotic arm to which the end effector is connected.

9. The medical navigation system according to claim 8, further comprising:
a mechanical interface located at the second end of the handle portion.

10. The medical navigation system according to claim 9, wherein the mechanical interface includes a dovetail interface with the scope clamp arm engaged therein and secured by a screw.

11. The medical navigation system according to claim 8, wherein the camera mount connected to the second end of the handle portion has a second camera mounted thereon, with a cable connected to the second camera extending through the cable cut-out.

12. The medical navigation system according to claim 11, wherein the second camera includes a situational awareness camera.

13. The medical navigation system according to claim 12, wherein the mating component connects to the output flange with a dowel pin and is secured with at least one screw.

14. The medical navigation system according to claim 13, wherein the trigger mechanism, the handle, a first camera, the second camera, the scope, the scope clamp arm, and the tracking marker frame all have respective center lines that are substantially aligned resulting in a thin profile that reduces obstruction of the view of a surgeon using the end effector in the medical navigation system.

* * * * *